United States Patent
Haar et al.

(10) Patent No.: US 8,328,735 B2
(45) Date of Patent: Dec. 11, 2012

(54) ANALYTICAL SYSTEM FOR DETECTING AN ANALYTE IN A BODY FLUID AND DISPOSABLE INTEGRATED PUNCTURING AND ANALYZING ELEMENT

(75) Inventors: Hans-Peter Haar, Wiesloch (DE); Joachim Hoenes, Zwingenberg (DE); Carina Horn, Biblis (DE); Andreas Poredda, Baar (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 919 days.

(21) Appl. No.: 12/105,596

(22) Filed: Apr. 18, 2008

(65) Prior Publication Data
US 2008/0262386 A1    Oct. 23, 2008

(30) Foreign Application Priority Data
Apr. 21, 2007   (EP) ..................... 07008167

(51) Int. Cl.
 *A61B 5/00* (2006.01)
 *A61B 17/14* (2006.01)
 *A61B 17/32* (2006.01)
 *B65D 81/00* (2006.01)
(52) U.S. Cl. .......... 600/583; 600/584; 606/181
(58) Field of Classification Search .............. 600/583, 600/573, 575, 584; 606/181–183
See application file for complete search history.

(56) References Cited

U.S. PATENT DOCUMENTS

| | | | |
|---|---|---|---|
| 4,627,445 A | 12/1986 | Garcia et al. | |
| 4,873,993 A | 10/1989 | Meserol et al. | |
| 5,871,494 A | 2/1999 | Simons et al. | |
| 5,951,492 A | 9/1999 | Douglas et al. | |
| 6,036,924 A | 3/2000 | Simons et al. | |
| 6,143,164 A | 11/2000 | Heller et al. | |
| 6,299,757 B1 | 10/2001 | Feldman et al. | |
| 2002/0164805 A1 | 11/2002 | Gaa et al. | |
| 2003/0050573 A1 | 3/2003 | Kuhr et al. | |
| 2003/0199790 A1* | 10/2003 | Boecker et al. | 600/576 |
| 2004/0064068 A1 | 4/2004 | DeNuzzio et al. | |
| 2004/0127818 A1 | 7/2004 | Roe et al. | |
| 2005/0021066 A1 | 1/2005 | Kuhr et al. | |
| 2005/0234368 A1* | 10/2005 | Wong et al. | 600/583 |
| 2005/0251064 A1 | 11/2005 | Roe | |
| 2006/0020228 A1 | 1/2006 | Fowler et al. | |

(Continued)

FOREIGN PATENT DOCUMENTS
EP   1 174 083 A2   1/2002
(Continued)

*Primary Examiner* — Max Hindenburg
*Assistant Examiner* — John Pani
(74) *Attorney, Agent, or Firm* — Woodard, Emhardt, Moriarty, McNett & Henry LLP (57) ABSTRACT

An analytical system for detecting an analyte in a body fluid comprises a disposable integrated puncturing and analyzing element and a reusable analytical system. The integrated element includes a puncturing element having a tip for generating a puncture wound in a body part and an elongated flat test strip having a top side and a bottom side. The integrated element is held in a holder such that, in a sample application position of the test strip, the top side of the test strip is facing upward. A sample application area for manual application of a drop exiting from the puncture wound of the body part is provided on the top side of the test strip such that, in the sample application position, the drop is applied to the sample application area from directly above.

12 Claims, 5 Drawing Sheets

U.S. PATENT DOCUMENTS

| | | |
|---|---|---|
| 2006/0079810 A1 | 4/2006 | Patel et al. |
| 2006/0200045 A1 | 9/2006 | Roe |

FOREIGN PATENT DOCUMENTS

| | | |
|---|---|---|
| EP | 1 189 064 A1 | 3/2002 |
| EP | 1 287 785 A1 | 3/2003 |
| EP | 1 402 812 A1 | 3/2004 |
| EP | 1 466 558 A2 | 10/2004 |
| WO | WO 2005/006985 A2 | 1/2005 |
| WO | WO 2005/102154 A2 | 11/2005 |
| WO | WO 2005/104949 A1 | 11/2005 |
| WO | WO 2005/107593 A1 | 11/2005 |
| WO | WO 2006/092281 A2 | 9/2006 |
| WO | WO 2006/108597 A2 | 10/2006 |

* cited by examiner

ANALYTICAL SYSTEM FOR DETECTING AN ANALYTE IN A BODY FLUID AND DISPOSABLE INTEGRATED PUNCTURING AND ANALYZING ELEMENT

CROSS REFERENCE TO RELATED APPLICATION

This application claims the benefit of European Patent Application No. 07 008 167.4 filed Apr. 21, 2007, which is hereby incorporated by reference in its entirety.

BACKGROUND

The present invention relates to an analytical system for detecting an analyte in a body fluid comprising a reusable analyzing instrument and a disposable integrated puncturing and analyzing element. The integrated puncturing and analyzing element has a puncturing element with a tip for generating a puncture wound in a body part and an elongated flat test strip which comprises a top side and a bottom side. The analyzing instrument has a housing, a holder for holding the integrated puncturing and analyzing element, and a coupling unit for coupling the puncturing element to a drive, said drive being adapted for driving a puncturing movement of the puncturing element during which a puncturing element is moved on a movement path, said puncturing movement including a forward phase in which the puncturing element is moved in a puncturing direction and a retraction phase during which the puncturing element is moved, after reaching a reversal point, opposite to the puncturing direction. The puncturing element is arranged parallel to the test strip and is movable on its movement path relative to the test strip.

For diagnostic purposes, small amounts of body fluids, such as blood, are removed from a body part, such as a tip of a finger. Puncturing instruments having lancets or puncturing elements are used for this purpose to generate a wound in a body part. The puncturing systems are provided such that they can be used by the patient or a caregiver.

After generating a puncture wound in the body part using the puncturing system, the body fluid must be applied to a test strip and transferred to an analytical system in a further step. Frequently, this will be a separate analytical system comprising an analyzing instrument and a disposable test strip. The analytical system is then used to detect the analyte of interest in the fluid.

Often, two separate instruments are used according to the state of the art; one as a puncturing instrument for generating the puncture wound, the other as an analyzing instrument for analyzing the body fluid of the puncture wound. The user thus has to operate two different instruments. After generating the puncture wound, he can mechanically squeeze the finger tip in order to increase the exit of blood from the finger. Only then does he touch the analyzing instrument to the puncture wound and take up a drop. This handling is strongly preferred by some users since they have full control over the action involved in blood collection and diagnosis. They are the ones determining how to puncture and how much blood to squeeze from the wound. The user thus willingly accepts, on the one hand, that more blood exits from the wound than absolutely necessary for analysis, and, on the other hand, that the systems get more contaminated.

The users find it advantageous to perform action sequences they trained to do and are familiar with, while having control over the analysis required for diagnosis including the blood collection. The two instruments, the puncturing instrument and the analyzing instrument, can be relatively simple systems which can be manufactured cheaply since each instrument needs to perform exactly only one function.

However, it is disadvantageous that one disposable element needs to be used in each of the systems, namely the lancet or the puncturing element in the puncturing system and the test strip having the analyzing element in the analytical system. Hence, the user is obliged to use and replace, procure and keep in stock two different consumable components. Moreover, the user is obliged to carry two instruments at all times.

For this reason, the state of the art shows that some effort has been made to improve the analysis of body fluids for the user. In the so-called compact instruments, the analyzing instrument and the puncturing instrument are integrated into a single instrument. Although the user has only a single instrument for the analysis, there is still a need to keep two different consumable elements in stock. The mechanical structure of such instruments is fairly complex. In many cases, they are considerably larger than the corresponding individual instruments. The use of cartridges is feasible only in the case of the test strips, but not the lancets. A combined analyzing instrument is described, e.g., in WO 2005/006985 A2.

Aside from this, much effort has been put into improving the analysis of body fluids with fully automatic systems which comprise an integrated puncturing and analyzing element having a test strip and a puncturing element. The exit point of the puncturing element and the reception point for the body fluid exiting a puncture wound are identical in these instruments. The blood, or the body fluid, is transferred from the wound by means of a capillary channel. The user places the instrument on his finger only once and then can read the analytical result directly after a time of analysis has elapsed. All intermediate steps are carried out by the instrument.

Many users do not accept fully automated instruments since they have no influence on the collection of blood and cannot recognize whether or not or how much blood was collected and how it is transported to the analyzing element. They do not wish to relinquish control over the individual operating steps to the system. Moreover, fully automated systems are expensive and complicated to manufacture.

SUMMARY OF THE INVENTION

An object of the present invention is therefore to propose an analytical system which, on the one hand, increases the operating convenience for the user and, on the other hand, allows the user to maintain full control over the individual steps of the procedure. Further, the instrument has to be cheap to manufacture.

The object is achieved by an analytical system with the features of claim 1 and by a disposable integrated puncturing and analyzing element with the features of claim 5. Preferred embodiments of the system and/or puncturing and analyzing element are defined in the dependent subclaims. The invention is also directed to a method with the features of claim 14.

In the context of the invention the detection of an analyte in a body fluid covers a qualitative and a quantitative detection. The analytical system according to the invention for detecting an analyte in a body fluid comprises a disposable integrated puncturing and analyzing element which includes a puncturing element having a tip for generating a puncture wound in a body part and an elongated flat test strip with a top side and a bottom side, and a reusable analyzing instrument with a housing which includes a holder for holding an integrated puncturing and analyzing element, and a coupling unit for coupling a puncturing element to a drive. The drive is adapted for driving a puncturing movement of the puncturing element.

During the puncturing movement, the puncturing element is moved on a movement path in the puncturing direction during a forward phase and, after having reached a reversal point of the puncturing movement, the puncturing element is moved opposite to the puncturing direction in a retraction phase. The puncturing element is arranged parallel to the test strip and movable relative to the test strip.

The integrated puncturing and analyzing element is held in the holder of the analyzing instrument such that, in a sample application position of the test strip, the top side of the test strip is facing upward. In addition, the integrated puncturing and analyzing element is positioned in the holder and the drive is arranged such that, in a puncturing position of the test strip, the tip of the puncturing element is moved beyond front end of the test strip which is in the direction of insertion, in order to generate a puncture wound in a body part. A sample application area for manual application of a drop from the puncture wound of the body part is provided on the top side of the test strip such that, in the sample application position, the drop is applied to the sample application area directly from above. The housing of the analyzing instrument is shaped to allow access to the sample application area of a test strip positioned in the sample application position. Moreover, the housing is also shaped to allow access to the front end of a test strip which is positioned in the puncturing position.

Referring to the housing, the analyzing instrument has a puncturing location at which the tip of the puncturing element generates a puncture wound in the body part, and an sample application location at which a drop from a puncture wound is applied to the sample application area directly from above. Applying the drop directly from above to the sample application area is understand as to apply the drop from above to the area and without any intermediate steps or transfer steps in which the drop is transferred to the sample application area. It is not limited to an application perpendicular to the sample application area.

The sample application location is different from the puncturing location. In the integrated puncturing and analyzing element employed, which is referred to as "dispo" hereinafter, the puncturing direction of the puncturing element and the direction from which the drop is applied to the sample application area are essentially perpendicular to each other. For this reason, the sample application location and the puncturing location are located at the housing at a distance from each other. Preferably, the sample application location and the puncturing location can be arranged on different sides of the housing, for example on sides of the housing which are perpendicular to each other, wherein preferably the sample application location is on top and the puncturing location is in front of the housing.

Using the analytical system according to the invention, the user positions his finger, which shall be representative of the body part hereinafter, at the puncturing location. Then, he carries out the puncturing movement of the puncturing element, whereby a puncture wound in the finger is generated. In a subsequent step, the user moves his finger from the puncturing location to the sample application location and applies the drop from the puncture wound to the sample application area directly from above. Since the puncturing location and the sample sample application location are spatially separated, the user needs to remove his finger from the instrument between the puncturing process and the analytical process. Between these two handling steps, i.e. the generation of the puncture wound and the application of a drop of blood to the sample application area, the user can, for example, squeeze his finger tip in order to increase the exit of blood from the puncture wound, if desired. The user maintains full control over the proceedings of the analysis and can intervene at any time. He determines the individual proceedings and steps of action.

Despite the separation of puncturing location and sample application location which the user is familiar with from the conventional two-instrument systems, the advantages of an integrated puncturing and analyzing element are maintained. The front end of the dispo in the puncturing direction provides a skin reference and/or skin contact surface. Prior to puncturing with the puncturing element, the finger can be tautened using of the skin contact surface such that the user's sensation of pain upon puncturing is reduced. Simultaneously, the puncturing element which is being moved parallel to the test strip can be guided, for example, through the dispo such that the puncturing motion is linear and in a straight line. This has a positive influence on the user's sensation of pain. In addition, the dispos are easy to store and keep in cartridges. The user has to store only one single consumable element, namely the dispo.

However, in contrast to fully automated analytical systems, there is no automatic transfer of the blood into the analytical system. This simplifies the analytical system design, and the analytical systems are therefore cheaper. A capillary channel in the puncturing element or in the test strip is unneeded, which leads to cost savings for the dispo and allows the dispos to be manufactured at a reasonable price.

The puncturing location is preferably arranged at a recess or opening of the housing through which the front end of the test strip being in the puncturing position is accessible. The user can either touch his finger directly to the opening or recess of the housing or to the front end of the test strip. In the first case, either the tip of the puncturing element moves through the recess and generates a puncture wound in the body part or the finger bulges through the recess into the inside of the housing. In the second case, the front end of the test strip extends through the recess of the housing. The front end of the test strip can preferably form a skin contact surface which places the skin in tension.

In a preferred embodiment, the housing comprises a recess to allow access to the sample application area and to the front end of the test strip. This so-called housing recess is sufficiently large for both the front end of the test strip and the sample application area being accessible to the user. Alternatively, the housing can provide two openings or recesses, one for allowing access to the sample application area and one for allowing access to the front end of the test strip. In this case the opening in front of the front end of the test strip can be formed to fit to a finger tip.

It is also preferred that the sample application position of the test strip and the puncturing position of the test strip are identical. This means that the dispo is held in the holder such that the test strip is both in the sample application position and in the puncturing position. The dispo is held in its holder and preferably not moved between the generation of a puncture wound and the application of the sample. It is self-evident that it is feasible to move, for example, the entire holder within the housing between generating the puncture wound and applying the sample to the sample application area. However, fixing the dispo in the holder is advantageous in that the dispo can be positioned very exactly, in particular in a case of photometric detecting of the analyte. The fixed dispo causes a very exact analyte detection which is associated with small permissible variation.

The exact fixing of the test strip in the holder is associated with another advantage: the position of the front end of the test strip is determined exactly. In a preferred embodiment, the front end of the test strip in the puncturing direction provides a skin contact surface that forms a puncturing depth reference element. A given puncturing depth value is determined by the distance in the puncturing direction between the skin contact surface and the position of the tip of the puncturing element at the reversal point of the puncturing movement. The simultaneous tensioning in the finger tip skin caused by the skin contact surface leads to exact control of the puncturing depth. This has a positive effect on the sensation of pain during puncturing.

Preferably, the sample application position is identical to the puncturing position. This common position can simultaneously be identical to an analyzing position, in which the analysis of the fluid applied to the sample application area takes place. The analyzing position can also be different from the other two positions.

In any case the analyzing position is in such, that an analysis can be performed by means of a measuring and analyzing unit of the instrument. In this respect, the invention is not limited to a particular arrangement. It can in particular be used with analysis systems operating on the basis of photometric/optical principles, but it is also suitable for other systems such as electrochemical analysis systems. In the former case the analysis position is such that a detection zone of the test strip (which can be identical with the sample application area but also can be different) is located at a location where it can be measured optically by an adjacent photometric device. In the case of an electrochemical measurement the analysis position has to be such that suitable electrical contact between electrodes of the test strip and an electrical measurement device of the instrument is possible.

BRIEF DESCRIPTION OF THE DRAWINGS

The invention is illustrated in more detail in the following based on the exemplary embodiments shown in the figures. Further features, forms, aspects and advantages of the invention will become apparent from the description and the drawings. The particularities presented therein can be used individually or in combination to create preferred embodiments of the invention. In the figures.

DESCRIPTION OF THE SELECTED EMBODIMENTS

Figure 1:
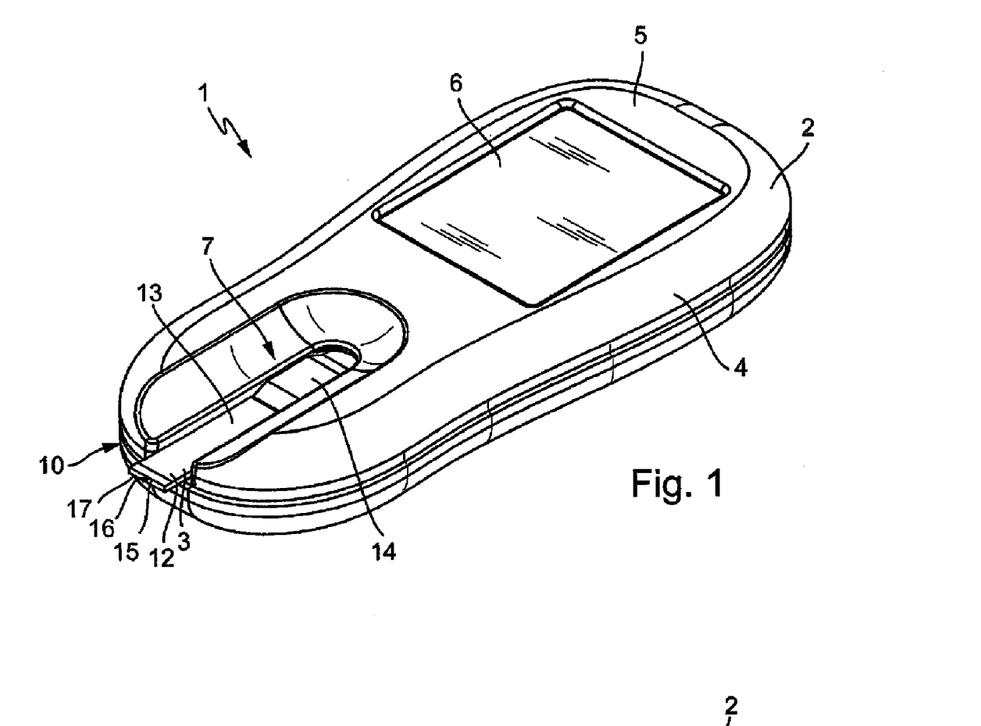
FIG. 1 shows an analytical system according to the invention having an analyzing instrument and an integrated puncturing and analyzing element.

FIG. 1 shows an analytical system 1 according to the invention comprising an analyzing instrument 2 and a disposable integrated puncturing and analyzing element which is referred to as dispo 3. The analyzing instrument 2 has a housing 4 with a top side 5. A display facility 6 is arranged at the top side 5 for displaying the result of a detection of an analyte in a body fluid.

The analyzing instrument 2 comprises in its housing 4 a housing recess 7 through which the dispo 3 is at least partly accessible. The housing recess 7 is designed to allow access to the front end of the dispo 3 The housing recess 7 extends from the top side 5 of the housing to a front side 10 of the housing 4.

Figure 2:
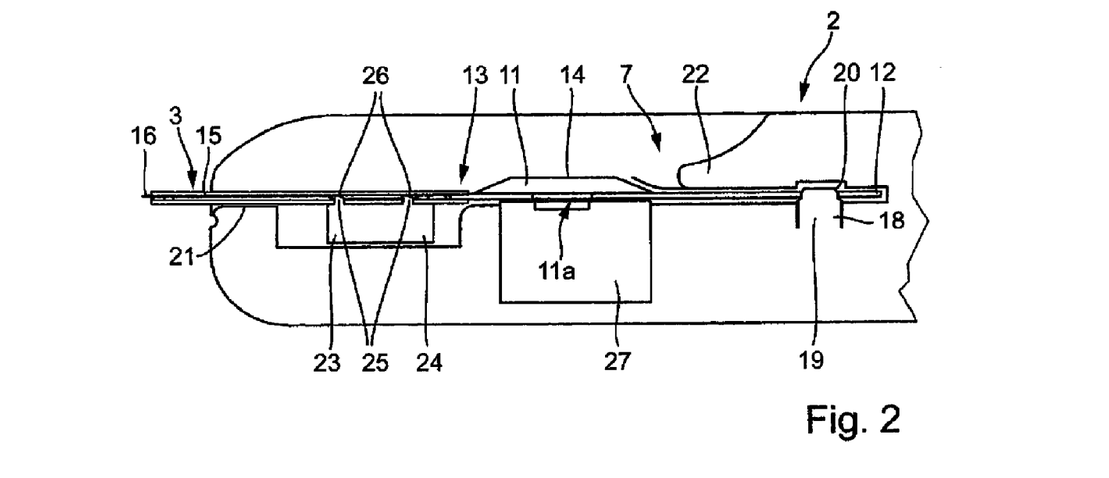
FIG. 2 shows a partial section through the analytical system of FIG. 1.

As is shown in more detail in FIGS. 3 to 5, the dispo 3 comprises a test strip 2 with a top side 13. A test pad 12 and a sample application area 14 are arranged on the top side 13 of the test strip 2, wherein the sample application area 14 is located on the cover surface of the test pad 12. The dispo 3 also comprises a puncturing element 15 having a tip 16, wherein the tip 16 of the puncturing element 15 can be moved beyond a front end 17 of the test strip 12 which is the end in the puncturing direction, in order to generate a puncture wound in a body part when the test strip 12 is arranged in the puncturing position (FIGS. 1 and 2). In the puncturing position, the front end 17 of the test strip 12 is accessible through the housing recess 7. A user can place his fingertip on the front end 17 in order to generate a puncture wound in the fingertip.

Simultaneously, the test strip 12 is arranged in a sample application position, in which the top side 13 of the test strip 12 is arranged such as to face upwards. The top side 13 of the test strip 12 is parallel to the top side 5 of the housing 4. In the sample application position of the test strip, the sample application area 14 is accessible through the housing recess 7 such that a drop exiting from the puncture wound can be applied to the sample application area 14 directly from above, i.e. it is moved from a direction perpendicular to the top side 5 or 13. Accordingly, the sample application area 14 is suitable for direct manual application of a drop of a body fluid, in particular of blood.

FIG. 2 shows part of a longitudinal section through the analyzing instrument 2 and the dispo 3 from FIG. 1. The dispo 3 is held in a holder 18 of the analyzing instrument 2. The holder 18 is provided in the form of holding pin 19 which engages through a bore hole 20 in the test strip 12 of the dispo 3. The dispo 3 is additionally supported by an edge 21 at the front end of the housing recess 7 such that the dispos 3 is arranged and positioned on the edge 21. An edge part 22 of the housing recess 7 presses from above against the top side 13 of the test strip 12 such that the dispo 3 is fixed in its position in the analyzing instrument 2.

A coupling unit 23 comprises a coupling element 24 for coupling to the puncturing element 15. The coupling element 24 is provided in the form of a drive side coupling structure 25 which engages an element side coupling structure 26 on the puncturing element 15 in a fitting fashion.

The drive side coupling structure 25 and the matching element side coupling structure 26 can be of any shape that allows force transmission from a drive of the analyzing instrument 2 to the puncturing element 15. The coupling element 24 engages the puncturing element 15 from below such that the puncturing element 15 is coupled to a drive (not shown) for driving a puncturing movement of the puncturing element 15.

A measuring and analyzing unit 27 is arranged within the analyzing instrument 2 such that the sample application area 14 of the dispo 3 is positioned above the measuring and analyzing unit 27 when the test strip 12 is located in the sample application position. In the exemplary embodiment shown, the measuring and analyzing unit 27 is a photometric unit. A photometrically detectable change occurs as a consequence of a reaction of a sample of a body fluid, which is contacted to the test pad 11, and a reagent contained in the test pad 11. This change is measured by the photometric unit.

In the embodiment shown, the sample application area 14 is a part of the test pad 11 (namely its upper side). The photometric detection preferably takes place at a detection zone 1a of the test field located at its bottom side (FIG. 2). Alternatively the sample application area can be provided at a certain distance from the section of the test strip where the detection zone is located. In this case the fluid sample can be transferred from the sample application area 14 to the respective reagent and detection zones by means of a capillary channel.

According to a further option the test strip may be an electrochemical biosensor in which case an electrochemical measuring and analyzing unit is suitably integrated into the analyzing instrument 2.

FIGS. 3 to 5 show various embodiments of a disposable integrated puncturing and analyzing element, dispo 3.

Figure 3A:
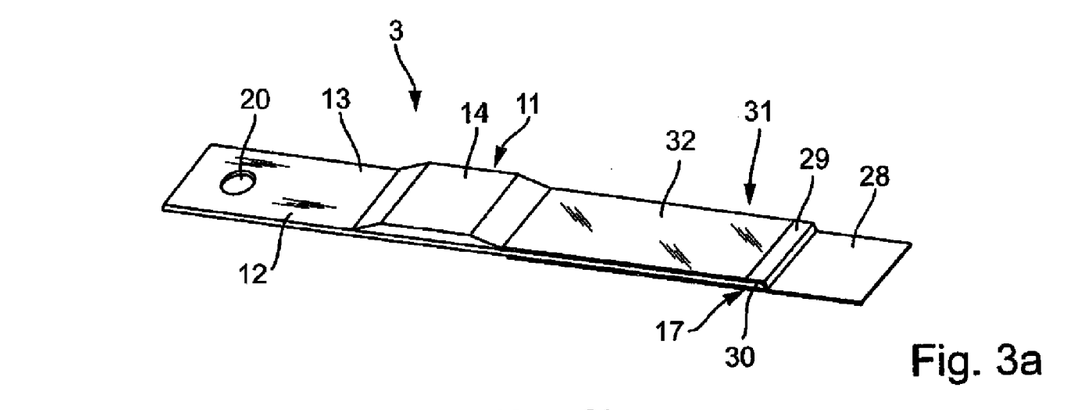
FIG. 3 shows a first embodiment of an integrated puncturing and analyzing element.

In FIG. 3a, the test strip 12 of the dispo 3 comprises on its back end in the puncturing direction a recess, which the holder of the analyzing instrument 2 can engage. The recess can be provided in the form of a bore hole 20, it can take any shape, but preferably it is round. Alternatively, instead of the bore hole 20, a holding structure can be provided to which a holder is engaged in order to fix the dispo 3 in its position in the analyzing instrument 2.

A protective film 28, for example a strip-off cover tape, comprises a protruding edge 39 for grasping by the user and a barrier 29. The film 28 is arranged at the front end 17 of the test strip 12 such that the barrier 29 touches on a front face 30 at the front end 17 of the test strip 12. The front face 30 is a skin contact surface 30a to which the user touches his finger. The skin contact surface 30a can be arranged and serve as puncturing depth reference element. The protective film 28 is part of a sterile protective sheath 31 which includes an upper cover film 32 and a lower cover film 33. Alternatively, a tape-like material or a foil, i.e. a plastic foil, can be used as a sheath. The sterile protective sheath 31 serves for sealing the puncturing element 15. The sterile protective sheath 31 is a primary packaging element of the dispo 3. The puncturing element 15 packaged in the sterile protective sheath 31 can be sterilized after sealing and then remains sterile for the entire time of storage of the dispo.

Figure 3B:
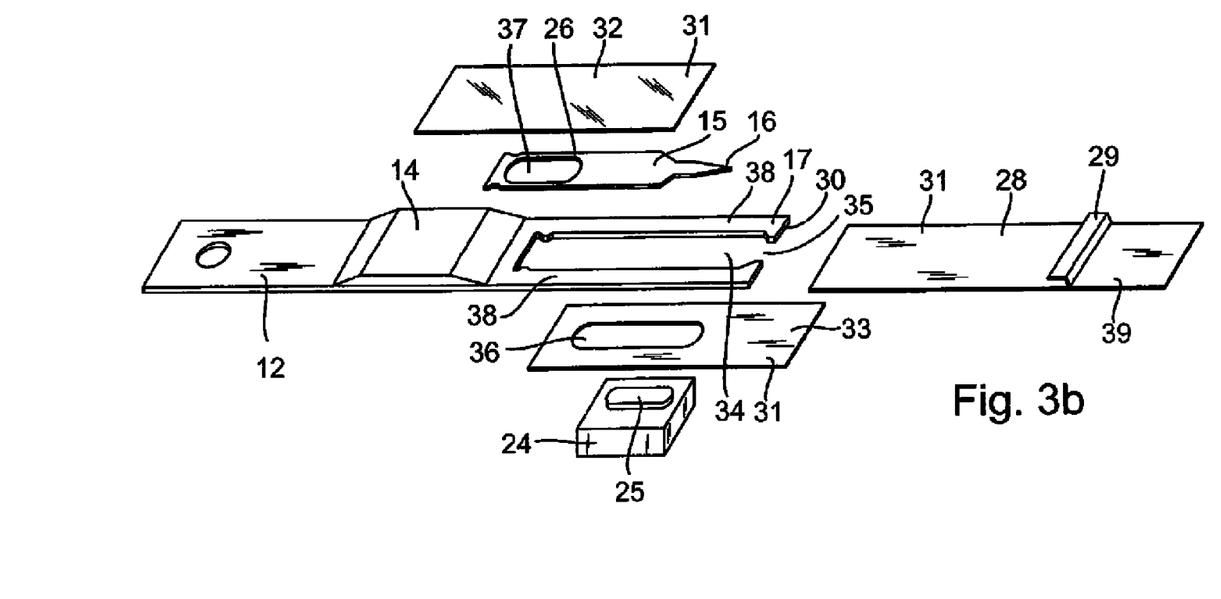

As is shown in the exploded view in FIG. 3b, the test strip 12 comprises a recess 34 in its front part. The puncturing element 15 is arranged in this preferred recess 34. In this preferred embodiment, the recess 34 is open towards the front end 17 of the test strip 12 such that the tip 16 of the puncturing element 15 can exit through a front orifice 35 of the recess 34 on its puncturing path and generate a puncture wound in a body part being in contact to the orifice 35.

The orifice 35 is closed-off by the barrier 29 of the protective film 28. Before the dispo 3 can be used, the protective film 28 with the barrier 29 is manually removed by a user by pulling the protective film 28 from the dispo 3 in the puncturing direction.

As soon as the protective film 28 is removed, the orifice 35 at the face 30 of the test strip 12 is open. Simultaneously, a recess and/or orifice 36 in the cover film 33 is also opened such that a coupling element 24 which is provided as a drive side coupling structure 25 for engaging with the puncturing element 15. The puncturing element 15 has a matching element side coupling structure 26 which is arranged as a coupling recess 37 for mutual coupling with the drive side coupling structure 25. The drive side coupling structure 25 extends through the orifice 36 of the lower cover film 33 into the coupling recess 37. The puncturing element 15 is then being coupled to the coupling element 24 such that the drive connected to the coupling element 24 can transmit force to the puncturing element 15 and drive it on its movement path.

The recess 36 in the lower cover film 33 must be adapted and arranged such that the drive side coupling structure 25 extending through it is not impeded when driving the puncturing element 15 on this path of movement.

The use of the dispo 3 according to FIG. 3 involves that the dispo 3 is first inserted into the analyzing instrument 2 and locked in place in the holder 18. Then the user pulls out the protective film 28 by its protruding edge 39 towards the front, whereby the barrier 29 is removed and the orifice 35 is released. Simultaneously, the engagement for the coupling unit 23 in the test element 15 is released. In the next step, the user presses his finger to the face 30 of the dispo 3, like in conventional puncturing instruments against the cap with an exit opening for the puncturing element. After the puncture, the user removes his finger from the analyzing instrument 2 and applies the puncture wound to the sample application area 14 of the dispo 3 from above such that a drop is transferred from the wound to the sample application area 14.

Preferably, the puncturing element 15 is surrounded by spacers 38 at least on its longitudinal sides with the thickness of the spacers being at least equal to the thickness of the puncturing element 15. Thickness is defined as the dimension perpendicular to the top side 13 of the test strip 12. If the thickness of the spacers 38 exceeds the thickness of the puncturing element 15 just a little, the puncturing element 15 can be clamped between the upper cover film 32 and the lower cover film 33 such that any independent movement is precluded. Using this so-called mild snap-in structure, the puncturing element 15 is snapped in place inside the sterile protective sheath 31 such that it cannot unintendedly move forward and damage the sterile protective sheath 31 during storage and transport of the dispo 3. After use of the dispo 3, the snap-in structure prevents the spent, contaminated tip 16 of the puncturing element 15 from penetrating the orifice 35. At the same time, the clamping pressure is not allowed to extend a predetermined pressure value to prevent any influence of the puncturing movement of the puncturing element 15.

Figure 4A:
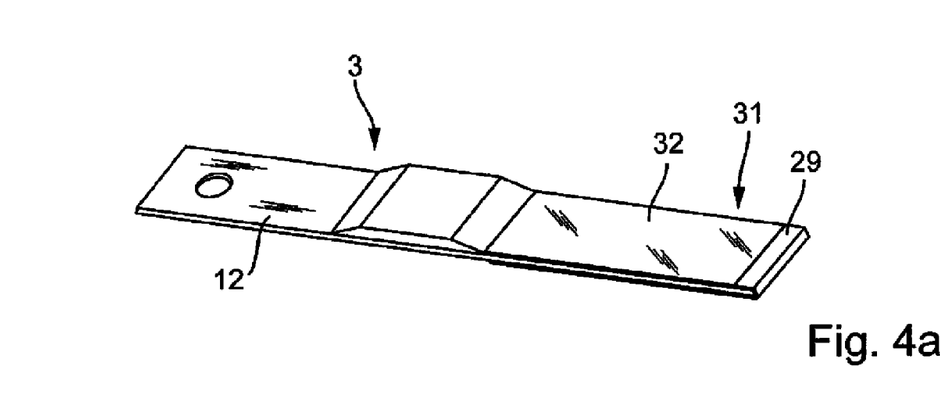
FIG. 4 shows a second embodiment of an integrated puncturing and analyzing element.
Figure 4B:
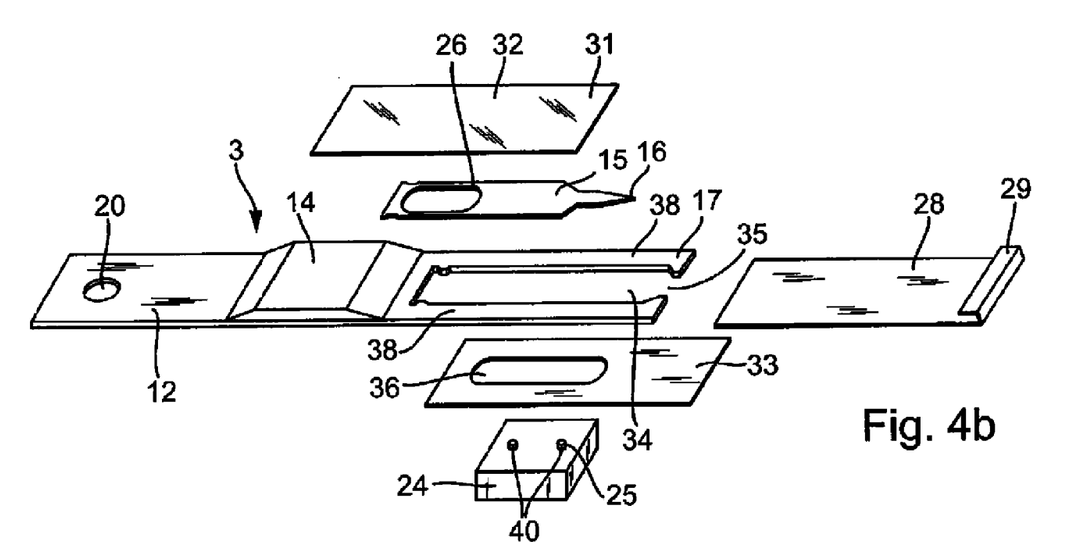

The FIGS. 4a,b show an alternative embodiment of the dispo 3. The protective film 28 does not comprise a protruding edge 39, but rather ends at barrier 29. Barrier 29 is adapted and arranged such that it can be perforated by the puncturing element 15 on its path of movement. Therefore, the dispo is ready for use right away and the user need not first remove the protective film 28 by pulling it out.

The drive side coupling structure 25 of the coupling element 24 is adapted and arranged such that the protective film 28 of the sterile protective sheath 31 is cut upon engagement through the orifice 36 of the lower cover film 33 into the element side coupling structure 26 of the puncturing element 15. In the example shown, the drive side coupling structure 25 comprises two sharp, knife-like pins 40 which cut the protective film 28. The sterile protective sheath 31 is preferably adapted in such a manner that the protective film 28 tears easily and continues to tear easily.

In the embodiments of the dispo shown in FIGS. 3 and 4, the sample application area 14 is arranged behind the puncturing element 15 in the puncturing direction. The sample application area 14 is located at a distance from the puncturing element 15 in both embodiments. However, an embodiment, in which the puncturing element 15 can protrude or extend at least partly under the sample application area 14 is also conceivable. However, the analysis of the fluid applied to the sample application area 14 must be feasible in the analyzing position of the test strip 12.

Figure 5A:
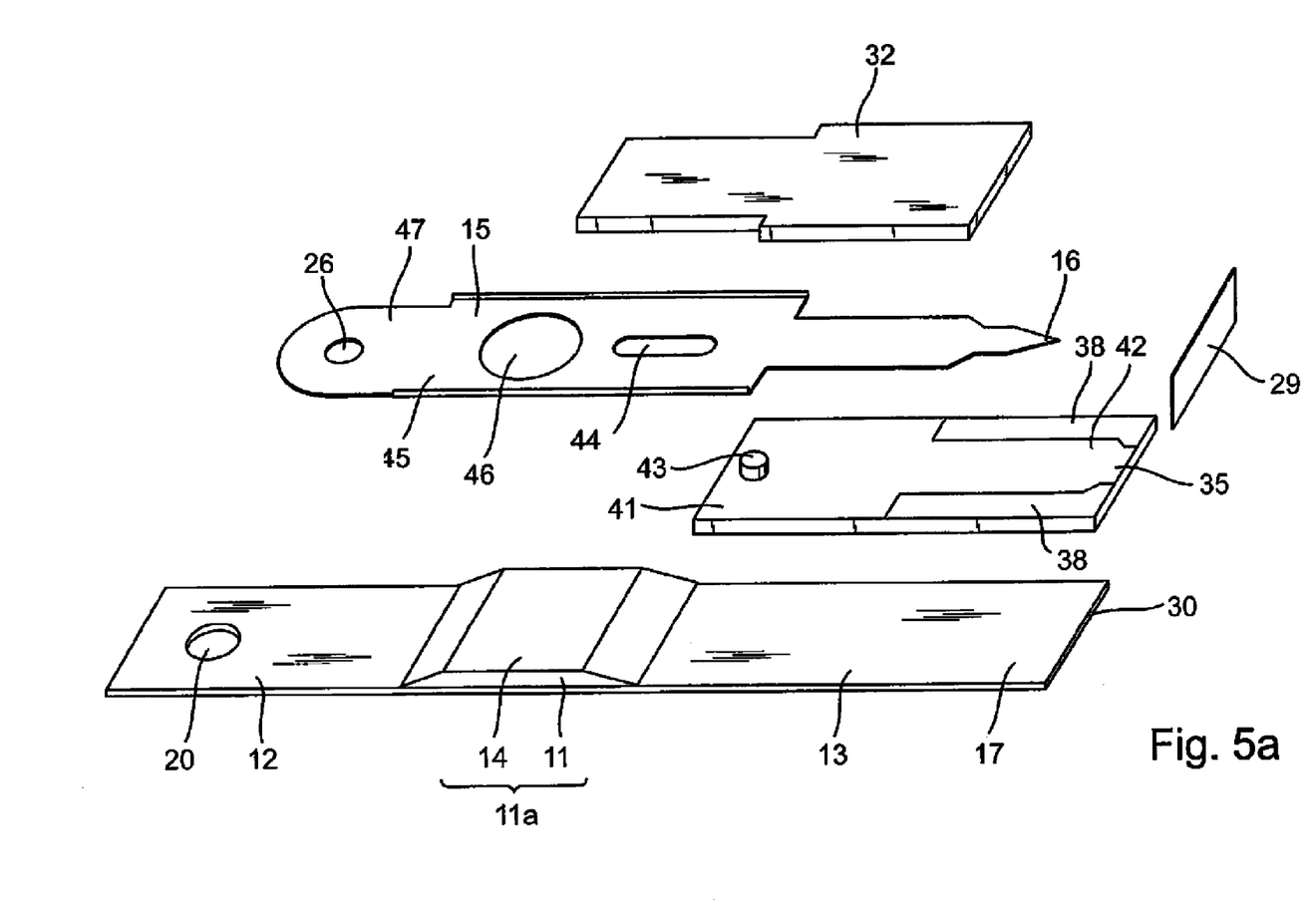
FIG. 5 shows a third embodiment of an integrated puncturing and analyzing element.
Figure 5B:
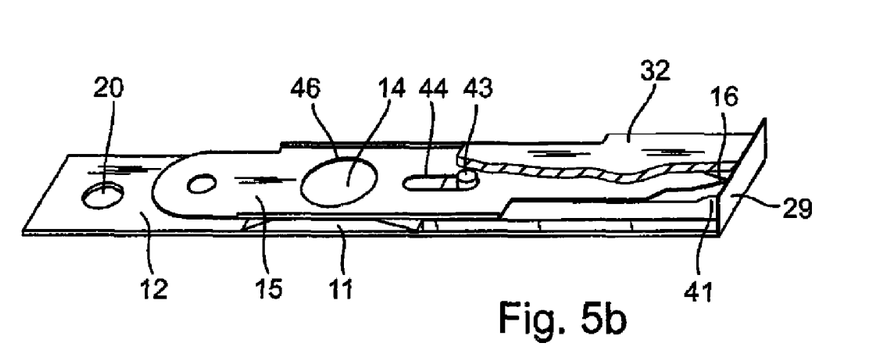
Figure 5C:
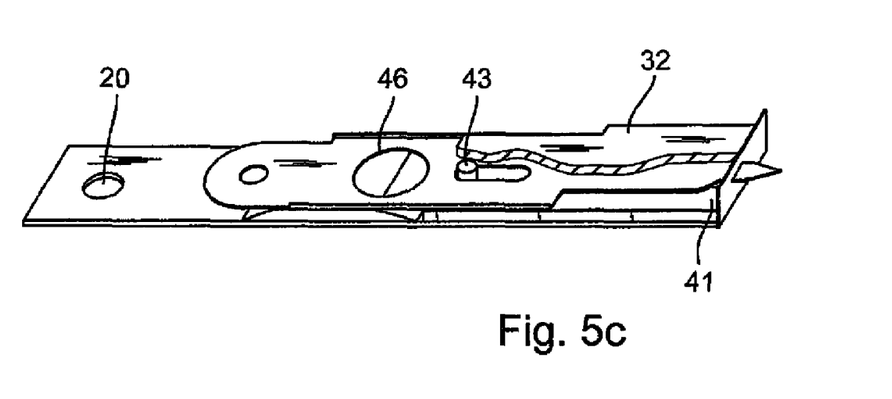

In a third embodiment of the dispo 3 shown in FIGS. 5a to 5c, the puncturing element 15 covers the sample application area 14. A lower guiding part 41, in which the puncturing element 15 is guided, is arranged on the top side 13 of the test strip 12 between the sample application area 14 and the front end 17 of the test strip 12. The thickness (dimension perpendicular to the top side 13) of the guiding part 41 is equal or larger by the thickness of the puncturing element 15 than the thickness of the test pad 11. The tip 16 of the puncturing element 15 is moved in a guiding channel 42 which comprises an orifice 35 on its front end. The guiding channel 42 is formed by two spacers 38 whose thickness is at least equal to the thickness of the puncturing element 15. The guiding part 41 comprises a guiding pin 43 which extends through a guiding recess 44 in the puncturing element 15.

The part of the puncturing element 15 which faces away from the tip 16 and is called cover part 45, is wider than the test pad 11 and the sample application area 14. Width is defined as the dimension transverse to the puncturing direction and transverse to the thickness. The width of the cover part 45 can be sufficiently large, if applicable, to also cover parts of the analyzing instrument 2 and protect them from getting contaminated by blood.

The cover part 45 of the puncturing element 15 comprises a transfer recess 46 which is called release hole or transfer orifice. Preferably, the transfer recess 46 is round, but it can be of any shape. It is arranged on the puncturing element 15 such that it is positioned above the sample application area 14 when the puncturing element 15 is positioned in a home position. In this position, the puncturing element 15 is retracted fully into the dispo 3 such that its tip 16 is arranged within the guiding channel 42, FIG. 5b. The puncturing element is at least at the end of the puncturing movement, i.e. after performing the puncture wound in the home position. The sample application area 14 is then accessible via the transfer recess 46.

The transfer recess 46 can be designed relatively small, i.e. clearly smaller than the width of the sample application area 14. Thus, the transfer recess 46 can be used as a so-called aiming aid which ensures that the blood is positioned in the middle of the sample application area 14 when applying small drops of blood. Combined with a location-resolving analytical optical set-up (optical measuring and analyzing unit), this arrangement allows even very small amounts of blood (less than one microliter) to be analyzed reliably.

As can be appreciated from FIGS. 5 a-c, the sterile protective sheath 31 is formed by the sterile lower guiding part 41, the upper cover film 32, and the barrier 29. The barrier 29 is perforated by the tip 16 of the puncturing element 15 proceeding on the path of movement. The barrier 29 is sufficiently high (dimension perpendicular to the top side 13) for it to cover the face 30 of the test strip 12, the front end of the lower guiding part 41 and the face of the upper cover film 32.

As a result, the puncturing element 15 is partly sealed by a sterile protective sheath 31 such that at least the tip 16 is maintained in sterile condition.

The puncturing element 15 comprises at its back end 47 in the puncturing direction an element side coupling structure 26 which can be engaged from above by the coupling element 24 of the coupling unit. The coupling unit 23 in the analyzing instrument 2 can be arranged above the dispo 3. It is advantageous in this embodiment that the front part of the dispo which is between the sample application area 14 and the front end 17 can be relatively short. This allows for the implementation of small dispos 3.

Another advantage of this embodiment of the dispo 3 is that a partial coverage of the sample application area 14 by the puncturing element 15 provides a hygienic function which prevents contamination of the instrument. Further, the puncturing element 15, the guiding part 41, the spacers 38, the upper film cover 32 and the barrier 29 may be manufactured as a sterile subassembly and joined to the non-sterile test strip as a final assembly operation. This allows use of analytical chemistry in the test pad 11 that is not compatible with sterilization processes, while maintaining the sterility of the portions of the dispo 3 that contact the patient.

The FIGS. 5b and 5c show the dispo 3 with partly sectioned upper cover film 32. FIG. 5b shows the test strip in the sample application position. The transfer orifice 46 is positioned directly above the sample application area 14. The tip 16 of the puncturing element 15 is fully retracted into the dispo 3. The guiding pin 43 of the lower guiding part 41 is arranged at the front end of the guiding recess 44.

FIG. 5c shows the arrangement of the dispo 3 if the puncturing element 15 is moved in the direction of the front end 17 of the test strip 12 such that the tip 16 protrudes fully from the dispo 3. The guiding pin 43 of the lower guiding part 41 is now arranged at the back end of the guiding recess 44 of the puncturing element 15 and limits the movement path of the puncturing element 15. This position corresponds to the reversal point of the puncturing movement. The sample application area 14 is now covered by the back end 47 of the puncturing element 15.

It is self-evident that it is conceivable to provide the puncturing element 15 such that the transfer recess 46 of the puncturing element 15 is arranged above the sample application area 14 only if the test strip 12 is located in the sample application position. In a home position, the transfer recess 46 could be positioned such that the sample application area 14 is concealed by the test strip 12.

What is claimed is:

1. An analytical system for detecting an analyte in a body fluid comprising a disposable integrated puncturing and analyzing element including a puncturing element having a tip for generating a puncture wound in a body part and including an elongated flat test strip having a top side and a bottom side, wherein the puncturing element defines a sample transfer orifice, and a reusable analyzing instrument including a housing which includes a holder for holding the integrated puncturing and analyzing element, a drive, and a coupling unit for coupling the puncturing element to said drive, said drive being adapted for driving a puncturing movement of the puncturing element during which the puncturing element is moved on a movement path, said puncturing movement including a forward phase in which the puncturing element is moved in a puncturing direction and a retraction phase during which the puncturing element is moved, after having reached a reversal point, opposite to the puncturing direction, wherein the puncturing element is arranged parallel to the test strip and the puncturing element is movable on a movement path relative to the test strip, the holder adapted for holding the integrated puncturing and analyzing element, in a sample application position of the test strip, in which the top side of the test strip faces upward, the holder and the drive adapted and arranged such that, in a puncturing position of the test strip, the tip of the puncturing element is moved beyond the front end of the test strip in the puncturing direction, in order to generate a puncture wound in a body part, wherein the puncturing element covers the sample application area when at the puncturing position, the sample application area located at the top side of the test strip such that, in the sample application position a drop of sample liquid from the puncture wound can be directly applied manually from above to the sample application area, wherein the sample transfer orifice is positioned directly above the sample application area when at the sample application position, and the housing being shaped to allow access to the sample application area of a test strip positioned in the sample application position.

2. The analytical system according to claim 1, characterized in that the front end of the test strip in a puncturing direction comprises a skin contact surface and serves as a puncturing depth reference element, whereby the puncturing depth is determined by a distance in the puncturing direction between the skin contact surface and a position of the tip of the puncturing element at the reversal point of the puncturing movement.

3. The analytical system according to claim 1, characterized in that the coupling unit comprises a coupling element for coupling to the puncturing element, said coupling element connecting to the test strip from the bottom side of the test strip.

4. The analytical system according to claim 1, wherein the puncturing element is at least partly covered by an upper cover film.

5. The analytical system of claim 1, further comprising:
the disposable integrated element including a lower guiding part having a guiding pin; and
the puncturing element having a guiding recess where the guiding pin is received.

6. A method for detecting an analyte in a body fluid comprising the steps of
providing an analytical system including
  a) a disposable integrated puncturing and analyzing element including a puncturing element having a tip for generating a puncture wound in a body part and including an elongated flat test strip having a top side and a bottom side, wherein the puncturing element defines a sample transfer orifice, and
  b) a reusable analyzing instrument with a housing which includes a holder for holding an integrated puncturing and analyzing element and with a coupling unit for coupling the puncturing element to a drive, said drive being adapted for driving a puncturing movement of the puncturing element during which the puncturing element is moved on a movement path, said puncturing movement including a forward phase in which the puncturing element is moved in a puncturing direction and a retraction phase during which the puncturing element is moved, after having reached a reversal point, opposite to the puncturing direction,
holding the disposable integrated puncturing and analyzing element in the holder such that the test strip is in a puncturing position, in which the puncturing element can be moved beyond the front end of the test strip,
coupling the drive to the puncturing element,
moving the puncturing element parallel to the test strip on a movement path beyond the front end of the test strip in the puncturing direction and generating a wound in a body part, which is positioned at a puncturing location in front of the front end of the test strip, wherein said moving the puncturing element includes moving the puncturing element to the puncturing location, wherein the puncturing element conceals the sample application area of the test strip when at the puncturing location,
moving the body part from the puncturing location to a sample application location, which is positioned above the test strip,
holding the disposable integrated puncturing and analyzing element such that the test strip is in the sample application position, in which the top side of the test strip faces upward and the sample application area located on the top side of the test strip is accessible,
moving the body part such that the puncture wound is above the sample application area of the test strip, while the test strip is in the sample application position,
manually applying a drop of sample liquid from the puncture wound directly from above to the sample application area, wherein during said manually applying the sample transfer orifice is positioned in such a manner to facilitate said manually applying the drop of the sample liquid directly from above to the sample application area,
detecting and analyzing the sample liquid applied to the sample application area by a measuring and analyzing unit.

7. An analytical system, comprising:
a disposable integrated element including
  a test element having a top side and an bottom side, the test element having a sample application area located on the top side of the test element,
  a puncturing element disposed over the top side of the test element to provide partial coverage of the sample application area, the puncturing element defining a sample transfer orifice, the puncturing element having a tip for generating a puncture wound and a back end, and
an analyzing instrument including a drive configured to actuate the puncturing element;
the drive being configured to move the puncturing element to a puncturing position where the puncture wound is generated, wherein the back end of the puncturing element covers the sample application area when at the puncturing position; and
the drive being configured to move the puncturing element from the puncturing position to a sample application position, the sample transfer orifice being positioned directly above the sample application area when at the sample application position to permit manual application of a drop of sample liquid from the puncture wound onto the sample application area.

8. The analytical system of claim 7, further comprising:
the disposable integrated element including a lower guiding part having a guiding pin; and
the puncturing element having a guiding recess where the guiding pin is received.

9. A method for detecting an analyte in a body fluid, comprising:
providing a disposable integrated element that includes a test element coupled to a puncturing element, wherein the test element has a top side and an bottom side, wherein the test element has a sample application area located on the top side of the test element, wherein the puncturing element is disposed over the top side of the test element, wherein the puncturing element defines a sample transfer orifice, wherein the puncturing element has a tip for generating a puncture wound;
creating a puncture wound by moving the puncturing element relative to the test element to a puncturing position, wherein the puncturing element conceals the sample application area when at the puncturing position;
moving the puncturing element relative to the test element from the puncturing position to a sample application position, wherein the sample transfer orifice is positioned directly above the sample application area when at the sample application position; and receiving a drop of sample liquid from the puncture wound onto the sample application area of the test element when the puncturing element is at the sample application position.

10. The method of claim 9, wherein:

the disposable integrated element includes has a guiding pin;

the puncturing element has a guiding recess where the guiding pin is received;

said creating the puncture wound includes positioning the puncturing element at the puncturing position by contacting the guiding pin against a back end of the guiding recess; and said moving the puncturing element relative to the test element from the puncturing position to the sample application position includes positioning the puncturing element at the sample application position by contacting the guiding pin against a front end of the guiding recess.

11. The analytical system of claim 10, further comprising:
the guiding recess having a front end and a back end;
the guiding recess being configured to have the guiding pin contact the front end of the guiding recess when the puncturing element is at the sample application position; and
the guiding recess being configured to have the guiding pin contact the back end of the guiding recess when the puncturing element is at the puncturing position.

12. The analytical system of claim 8, further comprising:
the guiding recess having a front end and a back end;
the guiding recess being configured to have the guiding pin contact the front end of the guiding recess when the puncturing element is at the sample application position; and
the guiding recess being configured to have the guiding pin contact the back end of the guiding recess when the puncturing element is at the puncturing position.

* * * * *

UNITED STATES PATENT AND TRADEMARK OFFICE
CERTIFICATE OF CORRECTION

PATENT NO. : 8,328,735 B2  
APPLICATION NO. : 12/105596  
DATED : December 11, 2012  
INVENTOR(S) : Hans-Peter Haar Page 1 of 1

It is certified that error appears in the above-identified patent and that said Letters Patent is hereby corrected as shown below:

Col. 13, line 6, replace "the disposable integrated element includes has a guiding" with
--the disposable integrated element includes a guiding--

Signed and Sealed this
Twelfth Day of February, 2013

Teresa Stanek Rea
*Acting Director of the United States Patent and Trademark Office*